(12) United States Patent
Fukuda et al.

(10) Patent No.: US 8,932,470 B2
(45) Date of Patent: Jan. 13, 2015

(54) FILTER MATERIAL FOR REMOVING AGGREGATES AND METHOD OF FILTERING BLOOD PRODUCT

(75) Inventors: Tatsuya Fukuda, Tokyo (JP); Yoshimasa Matsuura, Tokyo (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 857 days.

(21) Appl. No.: 12/936,253

(22) PCT Filed: Apr. 14, 2009

(86) PCT No.: PCT/JP2009/057476
§ 371 (c)(1),
(2), (4) Date: Oct. 4, 2010

(87) PCT Pub. No.: WO2009/128435
PCT Pub. Date: Oct. 22, 2009

(65) Prior Publication Data
US 2011/0031191 A1  Feb. 10, 2011

(30) Foreign Application Priority Data

Apr. 14, 2008 (JP) .................................. 2008-104574

(51) Int. Cl.
*B01D 11/00* (2006.01)
*B01D 61/00* (2006.01)
(Continued)

(52) U.S. Cl.
CPC .............. *B01D 39/02* (2013.01); *B01D 39/083* (2013.01); *A61M 1/3633* (2013.01);
(Continued)

(58) Field of Classification Search
None
See application file for complete search history.

(56) References Cited

U.S. PATENT DOCUMENTS 4,701,267 A * 10/1987 Watanabe et al. ............ 604/6.09
4,923,620 A    5/1990 Pall
(Continued)

FOREIGN PATENT DOCUMENTS

EP    0 606 646    7/1994
JP    01-236064    9/1989
(Continued)

OTHER PUBLICATIONS

World Health Organization, "Manual on the management, maintenance and use of blood cold chain equipment", 2005, pp. 1-91.*

(Continued)

*Primary Examiner* — Nam Nguyen
*Assistant Examiner* — Clare Perrin
(74) *Attorney, Agent, or Firm* — Greenblum & Bernstein, P.L.C.

(57) ABSTRACT

An aggregate-removing filter material efficiently removes aggregates that are contained in a blood product for transfusion and may cause transfusion reactions without clogging, and exhibits excellent quality stability, and a blood product filtration method uses a filter apparatus that includes the aggregate-removing filter material and a leukocyte-removing filter material. The aggregate-removing filter material includes short fibers having a fineness of 0.7 to 4.0 dtex and a fiber length of 1 to 80 mm, and a ground fabric that includes long fibers, a fiber axis of the long fibers being oriented in a planar direction of the ground fabric, the short fibers being entangled with the ground fabric so that the aggregate-removing filter material has a total weight per unit area of 10 to 80 g/m$^2$, and a layer of the short fibers forming a three-dimensional structure.

19 Claims, 1 Drawing Sheet

(51) Int. Cl.
*C02F 1/44* (2006.01)
*B01D 24/00* (2006.01)
*A01N 1/02* (2006.01)
*B01D 39/02* (2006.01)
*B01D 39/08* (2006.01)
*B01D 29/00* (2006.01)
*B01D 29/46* (2006.01)
*B01D 39/00* (2006.01)
*B01D 39/14* (2006.01)
*B01D 71/06* (2006.01)
*A61M 1/36* (2006.01)

(52) U.S. Cl.
CPC ............ *A61M 2205/7545* (2013.01); *B01D 2239/0421* (2013.01); *B01D 2239/0478* (2013.01); *B01D 2239/0609* (2013.01); *B01D 2239/0613* (2013.01); *B01D 2239/0618* (2013.01); *B01D 2239/0622* (2013.01); *B01D 2239/0627* (2013.01); *B01D 2239/0636* (2013.01); *B01D 2239/065* (2013.01); *B01D 2239/0659* (2013.01); *B01D 2239/0663* (2013.01); *B01D 2239/0668* (2013.01); *B01D 2239/086* (2013.01); *B01D 2239/1216* (2013.01); *B01D 2239/1225* (2013.01); *B01D 2239/1233* (2013.01)
USPC ...... 210/645; 210/651; 210/491; 210/500.27; 210/503; 210/505; 210/508; 435/2

(56) References Cited

U.S. PATENT DOCUMENTS

| | | | |
|---|---|---|---|
| 4,925,572 A | 5/1990 | Pall | |
| 4,976,861 A | 12/1990 | Pall | |
| 5,190,657 A | 3/1993 | Heagle et al. | |
| 6,048,464 A | 4/2000 | Tanaka et al. | |
| 6,267,898 B1* | 7/2001 | Fukuda et al. | 210/767 |
| 7,591,954 B2 | 9/2009 | Kimura et al. | |
| 7,597,806 B2 | 10/2009 | Uchi et al. | |
| 7,655,146 B2 | 2/2010 | Ozeki et al. | |
| 2001/0027946 A1 | 10/2001 | Fukuda et al. | |
| 2003/0175475 A1* | 9/2003 | Higgins et al. | 428/95 |
| 2004/0200775 A1* | 10/2004 | Fukuda et al. | 210/649 |
| 2004/0232067 A1* | 11/2004 | Simon | 210/500.36 |
| 2007/0029256 A1 | 2/2007 | Nakano et al. | |
| 2007/0175816 A1* | 8/2007 | Verpoort et al. | 210/490 |
| 2007/0199897 A1* | 8/2007 | Ozeki et al. | 210/645 |
| 2008/0010959 A1* | 1/2008 | Gillingham et al. | 55/486 |
| 2008/0011691 A1 | 1/2008 | Yamada et al. | |
| 2010/0252510 A1* | 10/2010 | Godsay et al. | 210/806 |

FOREIGN PATENT DOCUMENTS

| | | |
|---|---|---|
| JP | 03-173824 | 7/1991 |
| JP | 06-247862 | 9/1994 |
| JP | 07-67958 | 3/1995 |
| JP | 08-170221 | 7/1996 |
| JP | 08-291424 | 11/1996 |
| JP | 11-012182 | 1/1999 |
| JP | 2002-061023 | 2/2002 |
| JP | 2004-225184 | 8/2004 |
| JP | 2005-082939 | 3/2005 |
| WO | 97/23266 | 7/1997 |
| WO | 2005/014149 | 2/2005 |
| WO | WO 2006017703 A1 * | 2/2006 ............ B01D 29/00 |

OTHER PUBLICATIONS

Indian Examination Report issued with respect to counterpart Indian Application No. 2228/MUMNP/2010, dated Nov. 12, 2012.
International Search Report for PCT/JP2009/057476, mailed May 26, 2009.
International Preliminary Report on Patentability for PCT/JP2009/057476, mailed Dec. 9, 2010.
Taiwan Office action that issued in respect to patent family member Taiwanese Patent Application No. 10021163020, mail date is Dec. 23, 2011.

* cited by examiner

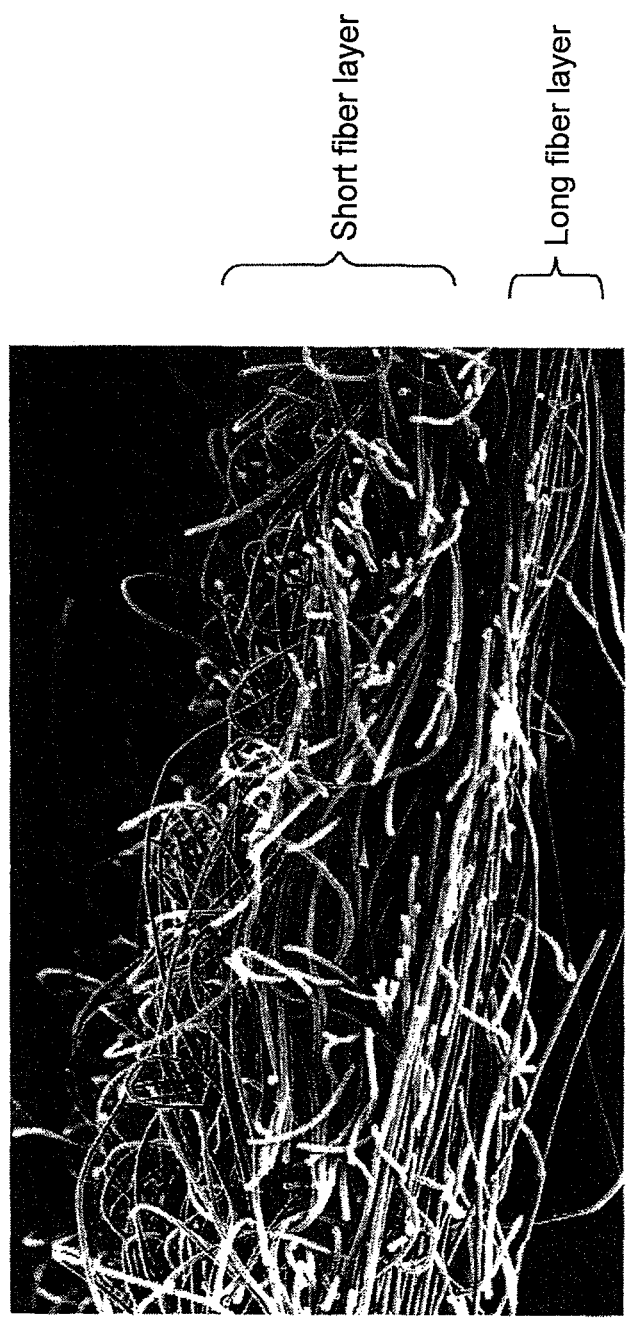

FILTER MATERIAL FOR REMOVING AGGREGATES AND METHOD OF FILTERING BLOOD PRODUCT

TECHNICAL FIELD

The present invention relates to a filter material for removing aggregates, and a method of treating a blood product using a filter apparatus that includes the filter material. Specifically, the invention relates to an aggregate-removing filter material that efficiently removes aggregates that are contained in a blood product for transfusion and may cause transfusion reactions, and a filtration method for removing the aggregates and leukocytes contained in a blood product using a filter apparatus that includes the aggregate- and leukocyte-removing filter material.

BACKGROUND ART

In recent years, leukocyte-free blood transfusion in which leukocytes contained in a blood product are removed in advance is increasingly applied in the field of blood transfusion. This is due to the finding that the side effects such as headache, nausea, chills, and an anhemolytic exothermic reaction, as well as heavy side effects such as alloantigen sensitization, viral infection, and post-blood transfusion graft-versus-host disease (GVHD) are mainly induced by leukocytes contained in blood products used for transfusion.

The methods for removing leukocytes from a blood product may be roughly classified into two kinds of methods of a centrifugal method in which leukocytes are separated and removed using a centrifuge by utilizing the difference in specific gravity among blood components, and a filtering method in which leukocytes are removed using a filter material formed of a fiber assembly, such as nonwoven fabric or the like, or a porous structure having continuous pores by utilizing adhesion of the leukocytes to the filter material or a sieve effect achieved by the pores of the filter material. Of these the filtering method has been widely used due to advantages such as simple operation, low cost, and excellent leukocyte-removing capability.

Most of the leukocyte-removing filter apparatuses which are now commercially available include a plurality of types of filter materials. An aggregate-removing filter material of loose texture that removes aggregates contained in a blood product is disposed in the upstream area near the blood inlet. A leukocyte-removing filter material of fine texture that removes leukocytes is disposed in the downstream area near the blood outlet side. Aggregates are formed by aggregating erythrocytes, leukocytes, platelets, fibrin, fibrinogen, other denatured proteins, fat globules and the like. Aggregates have diversity, including relatively small aggregates referred to as "microaggregates" having a size almost equal to that of leukocytes to about several tens of micrometers, and large aggregates referred to as "macroaggregates" having a size larger than about several tens of micrometers, for example exceed 1 mm, and the aggregates have high adhesion property. The number and the size of aggregates tend to increase as longer the storage period of the blood product and/or lower the storage temperature is. Therefore, when filtering a blood product using only a leukocyte-removing filter material without using an aggregate-removing filter material, the leukocyte-removing filter material clogs by aggregates, thereby being difficult to maintain the desired flow rate.

In order to deal with the above problem, Patent Document 1 discloses a filter apparatus that includes two or more types of aggregate-removing filter materials being selected from the group consisting of a nonwoven fabric, a woven fabric and a knitted fabric, and each having differ bulk density within the range of 0.1 to 1.0 g/cm$^3$ and the filter materials are disposed on the upstream side of a leukocyte-removing filter material so as to increase the bulk density of the aggregate-removing filter materials toward the downstream side.

Patent Document 2 discloses a filter apparatus that includes a plurality of types of fibers, wherein the product XY of the average fiber diameter X and the average fiber to fiber distance Y is specified. In Patent Document 2, a filter material with XY>50 is disposed upstream of the filter apparatus to capture relatively large aggregates, a filter material with 50≥XY>7 is disposed downstream of the filter material with XY>50 to capture relatively small aggregates, and a filter material with 7≥XY is disposed further downstream of the filter material with 50≥XY>7 to remove leukocytes.

Patent Document 3 discloses an aggregate-removing filter material that has at least two types of pore-groups including pore-group A having a pore size of 500 μm or more and an average pore diameter of 600 to 1500 μm and pore-group B having a pore size of 150 to 500 μm and an average pore diameter of 200 to 450 μm, and that the porosity of the filter material is 40% or more.

Patent Document 4 discloses a filter apparatus that includes the first to third elements, wherein the first element is a filter material that removes gel (which is synonymous word of large aggregates (macroaggregates)), the second element is a filter material that removes microaggregates, and the third element is a filter material that removes leukocytes.

PRIOR ART DOCUMENTS

Patent Document

Patent Document 1: JP-A-H03-173824
Patent Document 2: JP-A-H01-236064
Patent Document 3: JP-A-H07-67958
Patent Document 4: JP-A-H03-502094

DISCLOSURE OF THE INVENTION

Problems to be Solved by the Invention

The filter apparatuses including the aggregate-removing filter material disclosed in Patent Documents 1 to 3 can be used without problems when filtering a blood product that contains a small amount of aggregates. However, a significant decrease in filtration flow rate occurs due to clogging when filtering a blood product that is considered to contain a large amount of macroaggregates, such as a blood product that has been stored for a long time, a blood product that has been stored at a low temperature (lower than 4° C.), or a blood product which is prepared at a condition that an anticoagulant and blood are not sufficiently mixed after blood sampling. A situation in which filtration is stopped without completion may also often occur.

It is considered that the removal of the macroaggregates remains problems as described above, because the fibrous aggregate-removing filter materials used in Patent Documents 1 to 3 have a dense structure in which the fiber axis is oriented in the planar direction. Since a filter material having such a structure has a relatively small thickness and may be provided with high strength by embossing and the like, it is advantageous to produce on a large scale. However, when filtering blood that contains macroaggregates, aggregates remain near the surface of the filter material, and cause clogging.

On the other hand, the first element disclosed in Patent Document 4 is a relatively thick (thicker than about 3 to 5 mm) needlepunched nonwoven fabric that is formed of needle fibers obtained by mechanically entangling fibers by pushing a needle through them, and has a weight per unit area (metsuke) of greater than 70 g/m². In the examples of Patent Document 4, a needlepunched nonwoven fabric having a fiber diameter of 20 to 26 μm (corresponding to a fineness of 4.3 to 7.3 dtex) is used, and thus, the fibers may be not strongly entangled each other. Therefore, a change in fiber structure, such as tensile deformation, breakage or the like easily occurs. Such problem in quality that a brittle structure changes during filtering blood and the aggregate-removing efficiency becomes unstable may occur. In order to deal with this problem, the first element disclosed in Patent Document 4 is subjected to complex processing (e.g., hot pressing) when placing the first element in the filter apparatus. Though the shape of the first element can be maintained by hot pressing, the pore size of the filter material decreases, and the resistance to clogging by aggregates decreases.

As described above, an aggregate-removing filter material that has high resistance to clogging by aggregates and excellent quality stability (does not undergoes deformation) has not been proposed.

An object of the invention is to provide an aggregate-removing filter material that solves the above problems. Another object of the invention is to provide a method of filtrating a blood product that efficiently removes aggregates with various sizes and leukocytes contained in a blood product through the filtration of the blood product using a filter apparatus that an aggregate-removing filter material is disposed on the upstream side near the blood product inlet, and a leukocyte-removing filter material is disposed on the downstream side near the blood product outlet, and by utilizing gravity, a pump, or the like.

Means for Solving the Problems

The inventors conducted extensive studies in order to achieve the above objects. As a result, the inventors found that the above objects can be achieved by utilizing an aggregate-removing filter material that includes short fibers having a fineness of 0.7 to 4.0 dtex and a fiber length of 1 to 80 mm, and a ground fabric comprising long fibers, of which a fiber axis is oriented in a planar direction of the ground fabric, wherein the short fibers is entangled with the ground fabric so that the aggregate-removing filter material has a total weight per unit area of 10 to 80 g/m², and a layer of the short fibers forms a three-dimensional structure. This finding has led to the completion of the invention.

According to aspects of the invention, there is provided an aggregate-removing filter material for removing aggregates contained in a blood product, wherein the aggregate-removing filter material comprises short fibers having a fineness of 0.7 to 4.0 dtex and a fiber length of 1 to 80 mm, and a ground fabric comprising long fibers, of which a fiber axis is oriented in a planar direction of the ground fabric, wherein the short fibers are entangled with the ground fabric so that the aggregate-removing filter material has a total weight per unit area of 10 to 80 g/m², and a layer of the short fibers forms a three-dimensional structure. Furthermore, there is also provided a method of filtering a blood product using a filter apparatus that includes at least the aggregate-removing filter material and a leukocyte-removing filter material.

Effects of the Invention

According to the present invention, aggregates can be efficiently removed from a blood product by using the aggregate-removing filter material of the invention, even though the blood product contains a large amount of aggregates with various sizes, while preventing clogging due to aggregates. When filtering a blood product using a filter apparatus that simultaneously includes a leukocyte-removing filter material in addition to the aggregate-removing filter material by utilizing gravity, a pump, or the like, a decrease in filtration flow rate (ml/min) or an increase in pressure loss (Pa) with time due to clogging caused by aggregates can be suppressed, so that stable filtration can be carried out.

Moreover, the aggregate-removing filter material according to the invention has excellent shape stability. Specifically, since the aggregate-removing filter material according to the invention has sufficient strength to prevent occurrence of trouble such as structural deformation or the like during production thereof or filtration of a blood product, a stable aggregate-removing capability is obtained. Therefore, the quality of a filter apparatus that includes the aggregate-removing filter material according to the invention can be stabilized.

BRIEF DESCRIPTION OF THE DRAWINGS

FIG. 1 shows a cross-sectional electron micrograph of an aggregate-removing filter material exemplifying one embodiment of the invention.

DESCRIPTION OF EMBODIMENTS

Embodiments of the invention (hereinafter, referred to as "present embodiment(s)") are described in more detail below. Note that the invention is not limited to the following embodiments and various modifications may be carried out without departing from the scope of the invention.

An aggregate-removing filter material according to the present embodiment is one that is used to efficiently remove aggregates with various sizes that are contained in a blood product used for transfusion, such as whole blood product, a concentrated erythrocyte product, a concentrated platelet product or the like, and it is an aggregate-removing filter material including short fibers having a fineness of 0.7 to 4.0 dtex and a fiber length of 1 to 80 mm, and a ground fabric comprising long fibers, of which a fiber axis is oriented in a planar direction of the ground fabric, wherein the short fibers is entangled with the ground fabric so that the aggregate-removing filter material has a total weight per unit area of 10 to 80 g/m², and a layer of the short fibers forms a three-dimensional structure.

The aggregate-removing filter material according to the present embodiment is a filter material that is entangled the short fibers with the ground fabric comprising the long fibers, of which a fiber axis is oriented in the planar direction of the ground fabric. The term "ground fabric comprising long fibers" used herein refers to a sheet-shaped fiber mass wherein the fiber axis of almost all of the fibers including therein is oriented in the planar direction of the sheet. Specific examples of the ground fabric comprising long fibers can include a spunbonded nonwoven fabric obtained by forming a sheet using spunbond fibers formed by a spunbond method, a knitted fabric, and a woven fabric.

When using a spunbond nonwoven fabric, it is preferable to provide the spunbond nonwoven fabric with strength by moderate embossing.

It is preferable that long fibers that form a knitted fabric or a woven fabric have a twist constant (K) shown by the following expression (1) of 3,000 to 30,000, and preferably 5,000 to 10,000, from the viewpoint of strength and ease of entanglement with the short fibers. Since long fibers that form a knitted fabric or a woven fabric are normally produced by interlacing a plurality of fibers and twisting the resulting fibers, long fibers that form a knitted fabric or a woven fabric have very high strength.

$$\text{Twist constant } (K) = T \times D^{0.5} \quad (1)$$

T: twist number (turns/m), D: fineness (dtex)

Note that T is the twist number per unit length (m). D is the total fineness of multifilament yarn or a composite yarn of laminated multifilament yarn and another yarn.

The entanglement of the short fibers with the ground fabric comprising the long fibers will be described as follows. The short fibers are uniformly dispersed and layered on the ground fabric comprising the long fibers. Thereafter an external force is applied to the layered product to entangle short fibers with the long fibers or short fibers each other so as not to remove the short fibers from the ground fabric. The aggregate-removing filter material according to the invention is thus obtained. The short fibers may be layered on the ground fabric by means of carding, papermaking, or the like. When layering the short fibers on the ground fabric by papermaking, an appropriate surfactant or thickener is normally used to uniformly disperse the short fibers in water.

The short fibers may be entangled with the ground fabric comprising the long fibers by various methods known publicly, such as a thermal bonding method, a chemical bonding method, a needle punching method, a spunlace method, a steam jet method, and the like. Among these, a needle punching method and a spunlace method is preferable from the viewpoint of ease of processing, safety when used as a medical instrument, and the like.

In order to reduce the thickness of the finally formed filter material as much as possible so that the filter material can be easily placed in a filter apparatus, it is preferable to produce the filter material by a spunlace method (water jet punch method) that presses the short fibers into the ground fabric comprising the long fibers using a high-pressure water stream.

When producing the filter material according to the present embodiment using a spunlace method, the desired filter material can be obtained by setting the water pressure to 40 to 200 kgf/cm$^2$ and the diameter of the nozzle which jets out the water to 80 to 150 μm.

When entangling the short fibers with the ground fabric using a spunlace method, or the like, the fiber axis of the short fibers is oriented not only in the planar direction, but also in the longitudinal direction and diagonal directions. Moreover, the short fibers themselves become deformed to crimp-like shape due to external force (e.g., hydraulic pressure) so that some of the short fibers lose definite fiber axis orientation. As a result, the layer of the short fibers has a three-dimensional structure. Such a three-dimensional structure has a function of bringing large aggregates in the inside of the filter material and capturing the large aggregates, so that clogging of the filter material near the surface of the filter material by the large aggregates is reduced.

The ground fabric comprising the long fibers has a dense structure in which the fiber axis of the long fibers is oriented in the planar direction. Since the ground fabric comprising the long fibers that are entangled with the short fibers has very low fiber mobility as compared with the short fibers, the structure of the ground fabric is maintained even when subjected to a treatment such as a spunlace method, or the like. The ground fabric normally has a pore size smaller than that of the layer of the short fibers. It is considered that the ground fabric is effective for removing relatively small aggregates due to such a structure characteristic. Since the aggregate-removing filter material according to the invention is thus configured so that the layer of the short fibers removes large aggregates and the layer of the long fibers, which is a ground fabric, removes small aggregates, aggregate with various sizes can be efficiently removed by effectively utilizing the entire filter materials.

The term "three-dimensional structure" used herein refers to a structure in which the fiber axis of the short fibers is oriented in various directions, such as planar direction, longitudinal direction, diagonal directions and the like. FIG. 1 shows a cross-sectional photograph of a filter material, as an example of the aggregate-removing filter material according to the invention, which is obtained by layering short fibers on a spunbond long fiber layer and entangling the short fibers with the long fibers by a spunlace method. As is clear from the photograph, the fiber axis of the spunbond fiber layer which is ground fabric is oriented in the planar direction, and the fiber axis of the short fiber layer has a random orientation, that is, it does not have a definite orientation.

The presence or absence of a three-dimensional structure may be determined by the method described below. Specifically, first the thickness of the filter material is measured using such a photograph as shown in FIG. 1. The thickness thus measured is compared with the thickness of the filter material measured using a constant-pressure thickness meter that applies a constant load of 0.4 N per 1.8 cm$^2$. It is determined that a three-dimensional structure is formed by the short fiber layer when the thickness of the filter material measured using the constant-pressure thickness meter is smaller than the thickness of the filter material measured using the photograph by 10% or more, and preferably 30% or more. Since the three-dimensional structure formed by the short fibers is very soft and is easily compressed, the thickness of the filter material measured under a constant load is significantly smaller than the thickness of the filter material measured under no load. When measuring the thickness of the filter material using a photograph, in the case where the fibers in the surface area are unkempt and form random elevations and depressions so that it is difficult to determine the starting point for the measurement, the outermost surface area where a large number of fibers are present is determined to be the starting point, and the distance between one starting point and other starting point is measured as the thickness of the filter material. When measuring the thickness of the filter material using a photograph, the thickness of the filter material is measured three or more times at different points, and the average value of the measured values is taken as the thickness of the filter material. Similarly, when measuring the thickness of the filter material while applying a constant load, the thickness of the filter material is measured three or more times, and the average value of the measured values is taken as the thickness of the filter material.

The aggregate-removing filter material according to the invention includes the short fiber layer and the long fiber layer which is ground fabric, as described above. More specifically, the aggregate-removing filter material with a two-layer structure (short fiber layer-long fiber layer) in which the short fiber layer is layered on the long fiber layer, or the aggregate-removing filter material with a three-layer structure (short fiber layer-long fiber layer-short fiber layer) in which the long fiber layer is sandwiched by the short fiber layers can be given.

The short fibers used for the aggregate-removing filter material according to the present embodiment have a fineness of 0.7 to 4.0 dtex. If the short fibers have a fineness of less than 0.7 dtex, the so-called pore size formed by the short fibers is too small, so that the removal efficiency of large aggregates tends to decrease. If the short fibers have a fineness of more than 4.0 dtex, the short fibers may not be sufficiently entangled, so that the omission of the short fibers tends to increase. The fineness of the short fibers is preferably 1.0 to 2.4 dtex, and more preferably 1.2 to 1.8 dtex.

Note that the term "fineness" used herein refers to a value which can be calculated from the length and the weight of the fibers as defined in the Japan Industrial Standards (JIS) L 0104 and L 1013. Alternatively, when the fibers have an approximately columnar shape, the fiber diameter may be calculated by the following procedure, and may be converted into fineness using the fiber density ($g/cm^3$). Specifically, the fiber diameter is measured as follows, the filter material is first sampled at an arbitrary five or more points, and photographed using a scanning electron microscope and the like, at a magnification at which the fiber diameter can be measured. A grid sheet is superimposed on the photograph, and the diameters of one hundred or more fibers positioned at the grid points are measured. The term "diameter" used herein refers to the width of the fibers in the direction perpendicular to the fiber axis. A value (average value) obtained by dividing the sum of the diameters of the fibers thus measured by the number of fibers is taken as the fiber diameter, and the fineness may be calculated using the fiber diameter and the fiber density. However, the measured data is deleted when a plurality of fibers are overlapped each other, the fiber is hidden behind other fibers and the width of that fiber cannot be measured properly, when a plurality of fibers are melted to form a thick fiber, when a fiber with a diameter significantly differing from those of other fibers is present, or the like. When a plurality of types of fibers that differ in fiber diameter is mixed, the fineness of each type of fiber is calculated from the average fiber diameter of each type of fiber. If the fineness thus calculated is 0.7 to 4.0 dtex, such fibers are included within the scope of the short fibers according to the present embodiment. However, when the number of measurement fibers in question is 10% or less with respect to the total number of fibers, the fineness of such fibers is omitted from the target to be calculated the fineness.

The short fibers that may be used for the aggregate-removing filter material according to the present embodiment may have any cross-sectional shape, not limited to a circular cross-sectional shape. For example, the short fibers may have a modified cross-sectional structure disclosed in JP-A-H08-170221, JP-A-H08-291424, JP-A-2002-61023, JP-A-2004-225184, JP-A-2005-82939, or the like. It is preferable that the short fibers have a circular cross-sectional shape from the viewpoint of the dispersibility of the fibers when processing by using a high-pressure water stream and the high production efficiency of the fiber itself.

In the aggregate-removing filter material according to the present embodiment, the fineness of the long fibers that may be used as the ground fabric is not particularly limited insofar as the long fibers can be entangled with the short fibers. It is preferable that the long fibers have a fineness almost equal to that of the short fibers from the viewpoint of ease of entanglement. If the fineness of the short fibers is significantly lower than that of the long fibers, the short fibers may enter into the deep area of the ground fabric comprising the long fibers, so that it may be a risk that the large aggregate removal efficiency decreases. The other hand, if the fineness of the short fibers is excessively higher than that of the long fibers, the short fibers may not be sufficiently entangled, so that the short fibers may be omitted. Therefore, the ratio of the fineness of the long fibers to the fineness of the short fibers is preferably 1:0.5 to 1:2, and more preferably 1:0.8 to 1:1.5. It is particularly preferable to use long fibers and short fibers having an almost identical fineness.

When the aggregate-removing filter material according to the present embodiment has a three-layer structure (short fiber layer-long fiber layer-short fiber layer), and a short fiber layer (1), a long fiber layer, and a short fiber layer (2) are disposed in this order from the blood inlet side, it is preferable that the short fiber layers (1) and (2) have an identical fineness, or the fineness of the short fiber layer (1) is higher than that of the short fiber layer (2). Specifically, it is preferable that the fineness of the short fiber layer (1) is higher than that of the short fiber layer (2) by 1.0 times or more, and more preferably 1.5 times or more. Furthermore, as an ideal structure it may be preferable that the fineness of the fibers decreases in the following order: the short fiber layer (1)≥the long fiber layer≥the short fiber layer (2). In this case, large aggregates can be removed by the short fiber layer (1), and small aggregates can be removed by the long fiber layer and the short fiber layer (2) that are disposed on the downstream side.

The short fibers used for the aggregate-removing filter material according to the present embodiment have a fiber length of 1 to 80 mm. If the short fibers have a fiber length of less than 1 mm, the fibers may not be sufficiently entangled, so that the strength of the filter material tends to decrease. If the short fibers have a fiber length of more than 80 mm, the fiber components that are oriented in the longitudinal direction may be insufficient, so that the resistance characteristics to clogging due to aggregates tend to decrease. The fiber length of the short fibers is preferably 5 to 70 mm, and more preferably 20 to 60 mm.

The term "fiber length" used herein refers to a value obtained by photographing arbitrarily sampled short fibers, measuring the lengths of thirty or more short fibers having a definite starting point and end point using an image analysis system, or the like, and calculating the average value of the measured values.

It is preferable to crimp the short fibers in advance. Specifically, crimped fibers are easily entangled by a spunlace method as compared with straight fibers, and thus preferably contribute to an increase in strength.

The aggregate-removing filter material according to the present embodiment has a total weight per unit area of 10 to 80 $g/m^2$. If the aggregate-removing filter material has a total weight per unit area of less than 10 $g/m^2$, the removal efficiency or strength of the aggregate tends to decrease. If the aggregate-removing filter material has a total weight per unit area of more than 80 $g/m^2$, it may be difficult to place the aggregate-removing filter material in a filter apparatus. Moreover, when placing the aggregate-removing filter material in a filter apparatus together with a leukocyte-removing filter material and the like, the leukocyte-removing filter material may be compressed so that the filtration flow rate of a blood product may decrease. The total weight per unit area of the aggregate-removing filter material is preferably 15 to 60 $g/m^2$, and more preferably 20 to 50 $g/m^2$. The "total weight per unit area of the filter material" is determined by sampling three or more filter materials having an arbitrary size (e.g., 5 cm×5 cm) from a homogenous area and measuring the weight of the sampled filter material each, calculating the average value of the measured samples, and converting the resulting value into weight per square meter.

The ground fabric comprising the long fibers used for the aggregate-removing filter material according to the present embodiment has a weight per unit area of 5 $g/m^2$ or more, preferably 5 to 40 $g/m^2$, and more preferably 15 to 30 $g/m^2$. If the ground fabric comprising the long fibers has a weight per unit area of less than 5 g/m², the strength of the filter material may decrease.

The ratio of the weight per unit area of the ground fabric comprising the long fibers to the weight per unit area of the short fibers is preferably 1:0.1 to 1:10, and more preferably 1:0.8 to 1:3. When using a filter material having a three-layer structure, the sum of the weight per unit area of the short fibers on each side is preferably included within the above range with respect to the weight per unit area of the long fibers.

The aggregate-removing filter material according to the present embodiment preferably has a thickness of 0.1 to 1.0 mm. If the aggregate-removing filter material has a thickness of less than 0.1 mm, there is concern that a decrease in aggregate removal efficiency or strength may occur. If the thickness exceeds 1.0 mm, it may bring following trouble: the size of a filter apparatus must be increased when placing a plurality of filter materials, or a leukocyte-removing filter material placed on the downstream side of the aggregate-removing filter material is pressed and the density thereof may increase, so that the flow rate may decrease. The thickness of the aggregate-removing filter material is more preferably 0.2 to 0.8 mm, and still more preferably 0.3 to 0.6 mm. The thickness of the aggregate-removing filter material is measured as follows. Specifically, first the filter material is cut to a size of 5 cm×5 cm. The thicknesses of the sides (four portions), the corners (four portions), and the center (one portion) of the filter material are measured using a constant-pressure thickness meter, and the average value of the measured values is taken as the thickness of the filter material. The load applied by the constant-pressure thickness meter is 0.4 N, and the area of the measurement portion is 1.8 cm².

The aggregate-removing filter material according to the present embodiment preferably has a bulk density of 0.05 to 0.10 g/cm³. If the bulk density is less than 0.05 g/cm³, the aggregate removal efficiency and strength tend to decrease. If the bulk density is more than 0.10 g/cm³, the distance between the short fibers is small, and large aggregates may be thus captured by the surface of the filter material, so that the aggregate capture efficiency tends to decrease. The "bulk density of the filter material" is determined by cutting a sample having an arbitrary size (e.g., 5 cm×5 cm) from a homogenous area of the filter material, measuring the weight per unit area by the above method, that is, measuring the thickness of the center portion using a constant-pressure thickness meter, and dividing the weight per unit area by the thickness. In this case, the thicknesses of three or more samples cut from different portions are measured, and the average value of the measured values is taken as the bulk density of the filter material.

The aggregate-removing filter material according to the present embodiment preferably has an airflow resistance of 4 to 11 Pa·s·m/g. The term "airflow resistance" refers to a value measured as a differential pressure that occurs when passing air through the filter material at a constant flow rate. More specifically, the filter material is placed on an air hole having a diameter of 2.8 cm. A pressure loss (Pa·s/m) that occurs when flowing air (4 ml/s·cm²) through the filter material for 10 seconds or more is measured. The pressure loss is divided by the weight per unit area (g/m²) of the filter material, and the resulting value is multiplied by 10 to obtain the airflow resistance. A filter material having a large airflow resistance value allows air to pass through to only a small extent. It means that the filter material has a structure in which the fibers are densely entangled or that the filter material has a structure having a low porosity, that is, the filter material exhibits a property that a blood product flows through the filter material to only a small extent. Meanwhile, a filter material having a small airflow resistance value has a porous structure that includes a small number of fibers. Specifically, if the airflow resistance is higher than 11 Pa·s·m/g, it may take time to filter a blood product, or clogging may easily occur due to aggregates contained in a blood product. On the other hand, if the airflow resistance is lower than 4 Pa·s·m/g, aggregates may not be efficiently captured, so that the surface of a filter material disposed on the downstream may be clogged, or a decrease in strength may occur. The airflow resistance is more preferably 6 to 9 Pa·s·m/g.

The short fibers and the long fibers used for the aggregate-removing filter material according to the present embodiment may be formed of any material insofar as blood is not adversely affected. It is preferable that the short fibers and the long fibers be formed of a synthetic polymer from the viewpoint of high versatility, ease of processing, and low cost. Examples of the synthetic polymer include a polyamide, polyester, polyacrylonitrile, polyurethane, polyvinyl formal, polyvinyl acetal, polytrifluorochloroethylene, poly(meth) acrylate, polysulfone, polystyrene, polyethylene, polypropylene, cellulose, cellulose acetate, and the like. Among these, it is preferable to use a polyester, such as polyethylene terephthalate, polybutylene terephthalate or the like, due to high versatility and ease of the entanglement of fibers themselves by a spunlace method.

As described above, aggregates can be efficiently removed from a blood product that contains a large amount of aggregates with various sizes by utilizing the aggregate-removing filter material according to the present embodiment while preventing clogging due to aggregates.

The aggregate-removing filter material according to the present embodiment has a strength that substantially prevents a change in shape that causes a problem. This is because the short fibers having a fineness and a fiber length appropriate for the application are entangled with the ground fabric comprising the high-strength long fibers by a spunlace method, or the like. More specifically, when cutting the filter material to an arbitrary width, and stretching the filter material at a load of 0.4 N/cm, the elongation of the filter material is 3% or less. Therefore, since the filter material has a sufficient strength as described above, a change in shape rarely occurs when subjecting the filter material according to the present embodiment to various production steps, such as washing with water, heat treatment and the like, so that it is possible to realize stable production. Further, since a change in shape rarely occurs, stable aggregate capturing capability and excellent quality stability can be achieved.

When placing the aggregate-removing filter material according to the invention in a filter apparatus, the aggregate-removing filter material is disposed on the blood inlet side. Moreover, the short fiber layer is disposed on the blood inlet side, and the long fiber layer which is a ground fabric is disposed in the downstream thereof, that is, on the side of a leukocyte-removing filter material. When the aggregate-removing filter material has a three-layer structure (short fiber layer-long fiber layer-short fiber layer), the aggregate-removing filter material is preferably disposed so that the short fiber layer having a higher fineness is positioned near the blood inlet side.

A leukocyte-removing filter material is thus disposed on the downstream of the aggregate-removing filter material. The leukocyte-removing filter material used here may be either a porous structure having continuous pores, or a fiber structure having a very small fiber diameter. It is preferable to use a fiber structure (particularly a nonwoven fabric) as the leukocyte-removing filter material due to excellent productivity, inexpensiveness, and excellent quality stability.

When the leukocyte-removing filter material is a porous structure having continuous pores, as the material thereof, polyacrylonitrile, polysulfone, cellulose, cellulose acetate, polyvinyl formal, polyester, poly(meth)acrylate, polyurethane, or the like can be given. The pore size of the porous structure is preferably 3 to 25 µm. If the pore size of the porous structure is less than 3 µm, it may take time due to the passing resistance of a large amount of erythrocytes contained in a blood product through the leukocyte-removing filter material, so that there may unpreferably be at risk for elongating the processing time. If the pore size of the porous structure is more than 25 µm, the contact frequency of leukocytes with the porous structure may decrease, so that the leukocyte-removing capability may unpreferably decrease. The pore size of the porous structure is more preferably 5 to 15 µm. The term "pore size" used herein refers to the average flow pore size determined by the half dry method (ASTM E1294-89).

When the leukocyte-removing filter material is a fiber structure, a nonwoven fabric produced by a melt-blow method, a flash spinning method, a papermaking method, or the like, or a fiber structure formed of paper, a woven fabric, a knitted fabric, or the like, may be used. Among these, a nonwoven fabric having a very fine fiber diameter (i.e., having a large surface area) is preferable because the number of leukocyte adhesion points increases. As the material thereof synthetic fibers, such as polyamide, polyester, polyacrylonitrile, polytrifluoroethylene, polymethylmethacrylate, polystyrene, polyethylene, polypropylene or the like, regenerated fibers or purified fibers, such as cellulose or the like, semi-synthetic fibers, such as cellulose acetate or the like, natural fibers, such as hemp, cotton, silk or the like, or inorganic fibers, such as glass fibers or the like can be given. Among these, it is preferable to use synthetic fibers such as polyester, polypropylene, or polyethylene, or regenerated fibers or purified fibers formed of cellulose, from the viewpoint of ease of production, handling, and the like. Moreover, the fiber structure may be formed by fibers having an almost uniform diameter, or may be a material comingled a plurality of types of fibers that differ in fiber diameter, as disclosed in WO97/23266.

The fineness of the fiber structure used as the leukocyte-removing filter material is preferably 0.001 to 0.07 dtex (corresponding to a fiber diameter of 0.3 to 2.6 µm in the case of polyester fibers having a columnar cross-sectional shape). If the fineness of the fiber structure is less than 0.001 dtex, the fiber structure may not be stably produced due to low mechanical strength of the fibers. If the fineness of the fiber structure is more than 0.07 dtex, the leukocyte contact frequency may decrease, so that the leukocyte-removing capability may decrease. The fineness of the fiber structure is more preferably 0.003 to 0.03 dtex, and still more preferably 0.005 to 0.02 dtex. The fineness of the fiber structure (leukocyte-removing filter material) is determined in the same manner as the fineness of the aggregate-removing filter material.

The airflow resistance of the leukocyte-removing filter material is preferably 250 to 700 Pa·s·m/g. If the airflow resistance of the leukocyte-removing filter material is less than 250 Pa·s·m/g, the leukocyte-removing capability may be insufficient. If the airflow resistance of the leukocyte-removing filter material is more than 700 Pa·s·m/g, a sufficient blood filtration flow rate may not be achieved. The airflow resistance of the leukocyte-removing filter material is more preferably 350 to 600 Pa·s·m/g. The airflow resistance of the leukocyte-removing filter material is determined in the same manner as the airflow resistance of the aggregate-removing filter material.

The surface of the leukocyte-removing filter material or the aggregate-removing filter material may be modified in order to improve the affinity of a blood product to the filter material, or facilitate introduction of blood into a filter apparatus, for example. A polymer that includes a nonionic hydrophilic group and a basic nitrogen-containing functional group is suitable as the surface-modifying material. As a method of modifying the surface various methods publicly known such as a coating method, a plasma discharge method, an electron beam irradiation method, a radiation grafting method, and the like can be applied.

A container in which the filter material according to the invention is placed may be formed of a hard resin or a flexible resin. Examples of the hard resin include an acrylic resin, a silicon resin, an ABS resin, nylon, polyurethane, polycarbonate, vinyl chloride, polyethylene, polypropylene, a polyester, a styrene-butadiene copolymer, and the like. Among these, polycarbonate and a styrene-butadiene copolymer are preferable from the viewpoint of strength and versatility. It is particularly preferable to use a hard resin formed of polycarbonate due to excellent safety, high compression strength, and low denaturation during sterilization using γ-rays or high-pressure steam. In order to prevent insufficient blood filtration due to contact of the filter material with the container, it is preferable to provide a protrusion (so-called rib) having a height of 0.5 to 5.0 mm, preferably 1.5 to 3.0 mm, on the inner wall of the container on the blood product inlet side, so that a space is formed between the aggregate-removing filter material and the inner wall of the container on the blood product inlet side.

Examples of the suitable flexible resin that may be used to form the container include soft polyvinyl chloride, polyurethane, an ethylene-vinyl acetate copolymer, polyolefins such as polyethylene and polypropylene, a styrene-butadiene-styrene copolymer, a mixture of a thermoplastic elastomer and a softening agent such as a polyolefin or ethylene-ethyl acrylate, and the like. Among these, it is preferable to use soft vinyl chloride, polyurethane, an ethylene-vinyl acetate copolymer, a polyolefin, or a thermoplastic elastomer containing these materials as the main component. It is particularly preferable to use soft vinyl chloride or a polyolefin. When using the flexible resin, a sheet on which a blood product inlet is laid and a sheet on which a blood product outlet is laid are provided, and the filter material is sandwiched between these sheets. A technique such as high-frequency welding or the like is applied to the resulting product to form a filter apparatus. It is preferable to form concave/convex portion on the sheets on which the blood product inlet and the blood product outlet are laid respectively, so that a space having a dimension of 0.5 to 5.0 mm, and preferably 1.5 to 3.0 mm is formed between each sheet and the filter material, even though in the case of the filter apparatus comprising such a soft container.

Lastly, a method of filtering a blood product using a filter apparatus that includes the aggregate-removing filter material according to the invention and the above leukocyte-removing filter material is described below.

The aggregate-removing filter material according to the invention and the leukocyte-removing filter material are respectively disposed on a blood inlet side and a blood outlet side of a container that includes a blood product inlet and a blood product outlet to produce a filter apparatus. Another filter material may be placed between the aggregate-removing filter material and the leukocyte-removing filter material.

Specifically, one or more aggregate-removing filter materials are disposed in the container, and on the downstream thereof the leukocyte-removing filter material is disposed in an amount that leukocytes can be sufficiently removed. When filtering a whole blood product or a concentrated erythrocyte product that contains a large amount of leukocytes, the filter apparatus is loaded with about 0.2 to 1.0 g of the aggregate-removing filter material and about 4.0 to 7.0 g of the leukocyte-removing filter material. It is preferable to design the filter apparatus so that the filtration area (effective filtration cross-sectional area of the filter apparatus that filters a blood product) is 30 to 60 cm$^2$, and the internal volume (void volume of the filter apparatus) in a state in which the filter materials are disposed in the filter apparatus is 20 to 50 ml.

Soft tubes are connected to the blood inlet and the blood outlet of the filter apparatus thus completed. A bag (supply bag) that contains a blood product containing aggregates and leukocytes is connected to the end of one of the tubes, and a bag (recovery bag) that recovers the blood product filtered by the filter apparatus is connected to the end of the other tube. The blood product is filtered utilizing gravity, or filtered at a constant flow rate using a pump or the like. When filtering utilizing gravity, the supply bag is suspended at a height of 0.3 to 2.0 m from the recovery bag. When filtering at a constant flow rate, the flow rate may be set depending on the capability of the pump. It is preferable to filter the blood product at a flow rate of 10 to 100 ml/min from the viewpoint of the strength of the filter apparatus and prevention of problems, such as hemolysis or the like.

In the invention, the blood product to be filtered includes all blood products for transfusion, such as whole blood product, a concentrated erythrocyte product, a concentrated platelet product and the like. Of these, when a whole blood product or a concentrated erythrocyte product that is kept cold and contains a large amount of aggregates is applied to the invention, the invention practically achieves excellent effects. In particular, since a whole blood product or a concentrated erythrocyte product that has been stored at 1 to 6° C. for 12 to 80 hours contains a large amount of aggregates, the clogging resistance of the aggregate-removing filter material according to the invention is particularly remarkable.

The term "clogging resistance" effect to aggregates used herein means that a significant difference does not occur between the initial flow rate (g/min or ml/min) at the start of the filtration and the last filtration flow rate (g/min or ml/min) when almost the entire blood product has been filtered when filtering a blood product that contains aggregates using the filter apparatus. More specifically, the term "clogging resistance" means that the last filtration flow rate exhibits 0.5 or more with respect to the initial filtration flow rate. Alternatively, when filtering a blood product at a constant flow rate, the term "clogging resistance" means that the last pressure loss (Pa) at near completion of filtration is equal to or less than twice the initial pressure loss (Pa) at the start of the filtration. Note that the above clogging resistance standard is merely an example as a indication showing the clogging resistance, since the blood products have very large individual difference, and the filtration flow rate and the filtration pressure depend upon the temperature or the like.

When disposing the aggregate-removing filter material according to the present embodiment on the most upstream side of the leukocyte removal filter, clogging due to aggregates is prevented, so that a blood product can be filtered while maintaining a sufficient flow rate. A blood product that cannot be completely filtered should be normally discarded. Since the aggregate-removing filter material according to the present embodiment exhibits excellent clogging resistance, the blood product that contains a large amount of aggregates and has been discarded until now can be completely filtered without discarding it. This contributes to effective utilization of a valuable blood product, and it becomes very useful socially.

EXAMPLES

The present embodiments are further described below by way of examples. Note that the present invention is not limited to the following examples.

Experiment A

Evaluation of Filter Apparatus Including Only Aggregate-Removing Filter Material Having Two-Layer Structure Examples 1 to 3 and Comparative Examples 1 and 2

Aggregate-removing filter materials differing in the fineness of short fibers and the fineness of long fibers were produced by the following spunlace method. The weight per unit area, the thickness, and the airflow resistance of each aggregate-removing filter material were measured by the above methods. The elongation of each aggregate-removing filter material was also measured. Each aggregate-removing filter material was evaluated using a blood product.

A polyethylene terephthalate nonwoven fabric (15 g/m$^2$) produced by a spunbond method was used as a ground fabric comprising long fibers. Polyethylene terephthalate short fibers having a fiber length of 50 mm were placed on the nonwoven fabric (25 g/m$^2$). The fibers were entangled each other by jetting water to the resulting layered product at a pressure of 100 kgf/cm$^2$ from a nozzle having a diameter of 90 μm on a support net of a hydroentangling machine to obtain a filter material formed of a spunlaced nonwoven fabric (40 g/m$^2$).

Measurement of Elongation (Strength Test)

The filter material was cut to a width of 5 cm and a length of 10 cm, and placed in an autograph universal tester ("AG-1" manufactured by Shimadzu Corporation). The filter material was gradually stretched. The amount of elongation of the filter material in the longitudinal direction when stretched at 2 N (0.4 N/cm) was measured, and the elongation (%) was calculated by the following expression (2).

$$(\text{Longitudinal length after applying load}/10-1)\times 100(\%) \qquad (2)$$

Measurement of Flow Rate Change Ratio Using Blood Product

Twenty formed aggregate-removing filter materials were layered.

The layered product was placed in a polycarbonate container (effective filtration cross-sectional area: 25 cm$^2$ (5 cm×5 cm)) having a blood product inlet and a blood product outlet, and subjected to ultrasonic welding to obtain a filter apparatus. A rib having a height of 1.8 mm was laid on the inner wall of the blood product inlet side of the container, and a rib having a height of 0.6 mm was laid on the inner wall of the blood product outlet side of the container.

Human whole blood (400 ml) was sampled into a blood bag containing CPD as anticoagulant (56 ml) to prepare a whole blood product. The whole blood product was stored in a refrigerator at 2° C. for 48 hours. The whole blood product was connected to the above filter apparatus through a blood circuit provided with a clamp, a recovery bag for recovering the filtrated blood product was connected to the downstream thereof. The recovery bag was placed on a balance, and the blood product was filtered in a cold room at 4 to 6° C. and at a difference in elevation (head): 30 cm. After start of the filtration the time required for 50 g of the blood product to reach the recovery bag was measured, and the filtration flow rate (initial flow rate (g/min)) during this period was calculated. The time required for the amount of the blood product contained in the recovery bag to increase from 350 g to 400 g was then measured, and the filtration flow rate (final flow rate (g/min)) during this period was calculated. A value obtained by dividing the terminal flow rate by the initial flow rate was taken as the flow rate change ratio.

Evaluation of Aggregate-Removing Capability

The aggregate-removing capability of the filter material was evaluated as follows. The blood product contained in the recovery bag was sufficiently mixed, and 50 ml of the blood product was sampled from the recovery bag. The sampled blood product was filtered through a 40 micrometer mesh filter. After washing out unnecessary blood corpuscle components and the like using a physiological saline solution, the mesh filter used for filtration was observed using an optical microscope (magnification: 100 times). The full field was observed. When fine aggregates were captured by the mesh filter, it was determined that aggregates were present in the filtered blood product.

The property values of the aggregate-removing filter materials used in Examples 1 to 3 and Comparative Examples 1 and 2, and the evaluation results obtained using the blood product are summarized in Table 1.

ing filter materials used in Examples 4 to 6 were the same as the aggregate-removing filter materials used in Examples 1 to 3, and the aggregate-removing filter materials used in Comparative Examples 3 and 4 were the same as the aggregate-removing filter materials used in Comparative Examples 1 and 2. In Examples 7 to 14 and Comparative Examples 5 to 8 the aggregate-removing filter materials which were produced by changing the characteristic properties such as the fiber length of the short fibers, the fineness and the weight per unit area of the short fibers and the long fibers, and the like were used. The following leukocyte-removing filter materials were used. Two types of nonwoven fabric were prepared as the leukocyte-removing filter materials by a melt blow method. Specifically, one is a polyethylene phthalate nonwoven fabric (X) having a fineness of 0.032 dtex and a weight per unit area of 40 g/m², and another is a polyethylene phthalate nonwoven fabric (Y) having a fineness of 0.016 dtex and a weight per unit area of 40 g/m². The airflow resistances of these leukocyte-removing filter materials were 300 Pa·s·m/g (the filter material (X)) and 475 Pa·s·m/g (the filter material (Y)).

The aggregate-removing filter material and the leukocyte-removing filter materials (X and Y) were cut to dimensions of 7.4 cm×7.4 cm. Two leukocyte-removing filter materials (X) were placed on thirty-two leukocyte-removing filter materials (Y). Three aggregate-removing filter materials prepared by a spunlace method were placed on the uppermost leukocyte-removing filter material (X) so that the surface of the long fibers was positioned on the lower side. The filter materials thus layered were placed in a polycarbonate container having an inlet and an outlet so that the aggregate-removing

TABLE 1

|  |  | Example 1 | Example 2 | Example 3 | Comparative Example 1 | Comparative Example 2 |
|---|---|---|---|---|---|---|
| Short fiber | Fiber length | 50 | 50 | 50 | 50 | 50 |
|  | Fineness | 1.6 | 0.8 | 3.8 | 0.5 | 6.7 |
|  | Weight per unit area | 25 | 25 | 25 | 25 | 25 |
| Long fiber (ground fabric) | Fineness | 1.5 | 0.7 | 3.9 | 0.4 | 6.0 |
|  | Weight per unit area | 15 | 15 | 15 | 15 | 15 |
| Aggregate-removing filter material | Weight per unit area | 40 | 40 | 40 | 40 | 40 |
|  | Thickness | 0.56 | 0.54 | 0.59 | 0.50 | 0.64 |
|  | Airflow resistance | 8.6 | 10.2 | 7.6 | 12.3 | 3.5 |
|  | Bulk density | 0.071 | 0.074 | 0.068 | 0.080 | 0.063 |
| Elongation |  | <1 | <1 | <1 | <1 | <1 |
| Evaluation | Flow rate change ratio | 0.91 | 0.74 | 0.91 | 0.47 | 0.91 |
|  | Presence or absence of aggregates | Absent | Absent | Absent | Absent | Present |

Fiber length: mm,
Fineness: dtex,
Weight per unit area: g/m²,
Thickness: mm,
Airflow resistance: Pa · s · m/g,
Bulk density: g/cm³,
Elongation: %

Experiment B

Evaluation of Filter Apparatus Including Aggregate-Removing Filter Material Having Two-Layer Structure and Leukocyte-Removing Filter Material Examples 4 to 14 and Comparative Examples 3 to 8

Similarly to above Experiment A, polyethylene terephthalate short fibers were placed on a polyethylene terephthalate spunbond nonwoven fabric which was ground fabric comprising long fibers, and an aggregate-removing filter material was produced by a spunlace method. The aggregate-removfilter materials were disposed on the blood product inlet side, and subjected to ultrasonic welding to obtain a filter apparatus. The effective filtration area of the filter was 45 cm². A rib having a height of 1.8 mm was laid on the inner wall of the blood product inlet side of the container, and a rib having a height of 0.6 mm was laid on the inner wall of the blood product outlet side of the container. Only the aggregate-removing filter material was changed in Experiment B without changing the leukocyte-removing filter materials, the container, and the method of filtering the blood product at all.

A blood bag containing a whole blood product that was prepared in the same manner as in Experiment A and stored at 2° C. for 48 hours was connected to the blood inlet of the filter apparatus through a blood circuit provided with a clamp, and a recovery bag for recovering the filtrated blood product was connected to the downstream thereof. The recovery bag was placed on a balance, and the blood product was filtered at a difference in elevation (head): 1.4 m.

In addition to the measurement of the elongation of the aggregate-removing filter material and the flow rate change ratio, and the evaluation of the aggregate-removing capability (these measurement and evaluation were carried out in the same manner as in Experiment A), the residual leukocyte count was measured by the following method.

Measurement of Residual Leukocyte Count

The filtered blood product was sampled into a spitz tube made of polyethylene. After staining leukocytes in the sample using an acridine orange solution, the leukocyte concentration was measured using a fluorescent microscope. The residual leukocyte count in the recovery bag was calculated by multiplying the leukocyte concentration by the amount of the recovered blood product. If the residual leukocyte count is $10^6$ or less per recovery bag, the filter apparatus is considered to have a sufficiently high leukocyte removal performance.

The property values of the aggregate-removing filter materials used in Examples 4 to 14 and Comparative Examples 3 to 8, and the evaluation results obtained using the blood product were summarized in Table 2.

Comparative Examples 9 to 12

A filter apparatus was produced and evaluated in the same manner as in Example 4 using the same materials (leukocyte-removing filter material, container, and blood product) as in Example 4, except for using the following aggregate-removing filter material.

In Comparative Example 9, a filter material including only a ground fabric which comprised spunbond long fibers having the same fineness as that of Example 1 and having a weight per unit area of 40 g/m$^2$ was used as the aggregate-removing filter material.

In Comparative Example 10, a spunlaced nonwoven fabric including only short fibers having the same fineness and fiber length as those of Example 1 and having a weight per unit area of 40 g/m$^2$ was used as the aggregate-removing filter material.

In Comparative Examples 11 and 12, a nonwoven fabric produced by a needle punching method and including only short fibers was used as the aggregate-removing filter material. In Comparative Example 11, short fibers having the same fineness and fiber length as those of Example 1 and having a weight per unit area of 40 g/m$^2$ were used. In Comparative Example 12, short fibers having the same fineness and fiber length as those of Comparative Example 2 and having a weight per unit area of 40 g/m$^2$ were used.

The results obtained in Comparative Examples 9 to 12 are also summarized Table 2.

Example 15

An aggregate-removing filter material was prepared using spunbond polybutylene terephthalate long fibers (fineness: 1.7 dtex, weight per unit area: 15 g/m$^2$) and polybutylene terephthalate short fibers (fiber length: 50 mm, finenesses: 1.8 dtex, weight per unit area: 25 g/m$^2$). The filter apparatus in which as the aggregate-removing filter materials three above filter material were placed was evaluated in the same manner as in Example 4. The results are shown in Table 2.

Example 16

A filter apparatus was produced by disposing thirty-four leukocyte-removing filter materials (X) on the downstream side of the same aggregate-removing filter material as that of Example 4. The filter apparatus was evaluated in the same manner as in Example 4. The results are shown in Table 2.

Example 17

A filter apparatus was produced by disposing two leukocyte-removing filter materials (X) on the downstream side of the same aggregate-removing filter material as that of Example 4, and further disposing thirty-two leukocyte-removing filter materials (Z) having a fineness of 0.013 dtex, a weight per unit area of 40 g/m$^2$, and an airflow resistance of 600 Pa·s·m/g on the downstream side of the leukocyte-removing filter materials (X). The filter apparatus was evaluated in the same manner as in Example 4.

The results are shown in Table 2.

Example 18

A filter apparatus was produced by disposing one aggregate-removing filter material as that of Example 4, disposing three spunbond nonwoven fabrics having a weight per unit area of 30 g/m$^2$, an airflow resistance of 11.5 Pa·s·m/g, and a fineness of 1.6 dtex on the downstream side of the aggregate-removing filter material, and disposing two leukocyte-removing filter materials (X) and thirty-two leukocyte-removing filter materials (Y) on the downstream side of the spunbond nonwoven fabrics. The filter apparatus was evaluated in the same manner as in Example 4. The results are shown in Table 2.

Example 19

A concentrated erythrocyte product was filtered using the same filter apparatus as that of Example 18. The concentrated erythrocyte product (270 g, hematocrit level: 68%) used here was prepared by centrifuging sampled human whole blood (anticoagulant: CPD), and adding an MAP solution, which was an erythrocyte preservative, to the whole blood, and was stored at 4° C. for 72 hours. (270 g, hematocrit level: 68%) The filter apparatus was evaluated in the same manner as in Example 18, except that the difference in elevation (head) was set to 1.8 m, and the filtration flow rate during a period in which the amount of the blood product contained in the recovery bag increased from 170 g to 220 g was taken as the final flow rate. The results are shown in Table 2.

TABLE 2

|  |  | Example 4 | Example 5 | Example 6 | Comp. Example 3 | Comp. Example 4 | Example 7 | Example 8 | Example 9 | Example 10 |
|---|---|---|---|---|---|---|---|---|---|---|
| Short fiber | Fiber length | 50 | 50 | 50 | 50 | 50 | 20 | 75 | 50 | 50 |
|  | Fineness | 1.6 | 0.8 | 3.8 | 0.5 | 6.7 | 1.7 | 1.7 | 1.7 | 1.7 |
|  | Weight per unit area | 25 | 25 | 25 | 25 | 25 | 25 | 25 | 40 | 8 |

TABLE 2-continued

|  |  | | | | | | | | | |
|---|---|---|---|---|---|---|---|---|---|---|
| Long fiber (ground fabric) | Fineness | 1.5 | 0.7 | 3.9 | 0.4 | 6.0 | 1.7 | 1.7 | 1.7 | 1.7 |
|  | Weight per unit area | 15 | 15 | 15 | 15 | 15 | 15 | 15 | 35 | 6 |
| Aggregate-removing filter material | Weight per unit area | 40 | 40 | 40 | 40 | 40 | 40 | 40 | 75 | 14 |
|  | Thickness | 0.56 | 0.54 | 0.59 | 0.50 | 0.64 | 0.51 | 0.42 | 0.86 | 0.19 |
|  | Airflow resistance | 8.6 | 10.2 | 7.6 | 12.3 | 3.5 | 8.9 | 10.2 | 10.1 | 8.5 |
|  | Bulk density | 0.071 | 0.074 | 0.068 | 0.080 | 0.063 | 0.078 | 0.095 | 0.087 | 0.074 |
| Elongation |  | <1 | <1 | <1 | <1 | <1 | <1 | <1 | <1 | 2.8 |
| Evaluation | Flow rate change ratio | 0.85 | 0.66 | 0.63 | 0.39 | 0.29 | 0.79 | 0.68 | 0.69 | 0.58 |
|  | Presence or absence of aggregates | Absent | Absent | Absent | Absent | Absent | Absent | Absent | Absent | Absent |
|  | Residual leukocyte count | $<10^5$ | $<10^5$ | $<10^5$ | $<10^5$ | $<10^5$ | $<10^5$ | $<10^5$ | $<10^5$ | $<10^5$ |

|  |  | Example 11 | Example 12 | Example 13 | Example 14 | Comp. Example 5 | Comp. Example 6 | Comp. Example 7 | Comp. Example 8 | Comp. Example 9 |
|---|---|---|---|---|---|---|---|---|---|---|
| Short fiber | Fiber length | 50 | 50 | 50 | 50 | 0.5 | 90 | 50 | 50 | — |
|  | Fineness | 1.7 | 3.4 | 1.7 | 1.7 | 1.7 | 1.7 | 1.7 | 1.7 | — |
|  | Weight per unit area | 25 | 25 | 8 | 40 | 25 | 25 | 3 | 20 | — |
| Long fiber (ground fabric) | Fineness | 3.2 | 1.8 | 1.7 | 1.7 | 1.7 | 1.7 | 1.7 | 1.7 | 1.5 |
|  | Weight per unit area | 15 | 15 | 40 | 8 | 15 | 15 | 5 | 80 | 40 |
| Aggregate-removing filter material | Weight per unit area | 40 | 40 | 48 | 48 | 40 | 40 | 8 | 100 | 40 |
|  | Thickness | 0.59 | 0.46 | 0.41 | 0.71 | 0.35 | 0.39 | 0.10 | 0.78 | 0.32 |
|  | Airflow resistance | 7.6 | 9.6 | 10.3 | 6.3 | 11.3 | 13.2 | 9.1 | 9.4 | 11.3 |
|  | Bulk density | 0.068 | 0.087 | 0.117 | 0.068 | 0.114 | 0.103 | 0.080 | 0.128 | 0.125 |
| Elongation |  | <1 | <1 | <1 | 2.2 | <1 | <1 | 4.3 | <1 | <1 |
| Evaluation | Flow rate change ratio | 0.68 | 0.59 | 0.65 | 0.74 | 0.45 | 0.38 | 0.33 | 0.34 | 0.11 |
|  | Presence or absence of aggregates | Absent | Absent | Absent | Absent | Absent | Absent | Absent | Absent | Absent |
|  | Residual leukocyte count | $<10^5$ | $<10^5$ | $<10^5$ | $<10^5$ | $<10^5$ | $<10^5$ | $<10^5$ | $<10^5$ | $<10^5$ |

|  |  | Comp. Example 10 | Comp. Example 11 | Comp. Example 12 | Example 15 | Example 16 | Example 17 | Example 18 | Example 19 |
|---|---|---|---|---|---|---|---|---|---|
| Short fiber | Fiber length | 50 | 50 | 50 | 50 | 50 | 50 | 50 | 50 |
|  | Fineness | 1.6 | 1.6 | 6.7 | 1.8 | 1.6 | 1.6 | 1.6 | 1.6 |
|  | Weight per unit area | 40 | 40 | 40 | 25 | 25 | 25 | 25 | 25 |
| Long fiber (ground fabric) | Fineness | — | — | — | 1.7 | 1.5 | 1.5 | 1.5 | 1.5 |
|  | Weight per unit area | — | — | — | 15 | 15 | 15 | 15 | 15 |
| Aggregate-removing filter material | Weight per unit area | 40 | 40 | 40 | 40 | 40 | 40 | 40 | 40 |
|  | Thickness | 0.59 | 3.10 | 3.30 | 0.53 | 0.56 | 0.56 | 0.56 | 0.56 |
|  | Airflow resistance | 7.8 | 3.2 | 2.9 | 7.6 | 8.6 | 8.6 | 8.6 | 8.6 |
|  | Bulk density | 0.068 | 0.013 | 0.012 | 0.075 | 0.071 | 0.071 | 0.071 | 0.071 |
| Elongation |  | 4.6 | 12.3 | 21.4 | <1 | <1 | <1 | <1 | <1 |
| Evaluation | Flow rate change ratio | 0.47 | 0.44 | 0.37 | 0.78 | 0.81 | 0.77 | 0.90 | 0.84 |
|  | Presence or absence of aggregates | Absent | Absent | Absent | Absent | Absent | Absent | Absent | Absent |
|  | Residual leukocyte count | $<10^5$ | $<10^5$ | $<10^5$ | $<10^5$ | $8 \times 10^5$ | $<10^5$ | $<10^5$ | $<10^5$ |

Fiber length: mm,
Fineness: dtex,
Weight per unit area: g/m$^2$,
Thickness: mm,
Airflow resistance: Pa · s · m/g,
Bulk density: g/cm$^3$,
Elongation: %

Experiment C

Evaluation of Filter Apparatus Including Aggregate-Removing Filter Material Having Three-Layer Structure and Leukocyte-Removing Filter Material Examples 20 to 24 and Comparative Examples 13 to 16

A multifilament made of polyethylene terephthalate was obtained by drawing an undrawn filament obtained by spinning at a temperature of 270° C. and a speed of 1500 m/min. the multifilament was twisted and then processed to a woven fabric to be taken as a ground fabric.

Polyethylene terephthalate short fibers were dispersed in water, and layered on each side of the ground fabric by a papermaking method. The short fibers were entangled with the ground fabric and other short fibers by jetting water at a pressure of 100 kgf/cm$^2$ from a nozzle with a diameter of 150 μm to obtain an aggregate-removing filter material having a three-layer structure.

The elongation of the aggregate-removing filter material was measured in the same manner as in Example 1 as a strength thereof. The evaluation of the resulting filter apparatus using the blood product was carried out in the same manner and condition as in Example 4. The aggregate-removing filter material was disposed so that a short fiber layer (1) was positioned on the blood product inlet side and a short fiber layer (2) was positioned on the side of a leukocyte-removing filter material, and the leukocyte-removing filter material was disposed on the blood product outlet side.

The results of the tests of the property values, the elongation, and the aggregate clogging resistance (flow rate change ratio) of the aggregate-removing filter materials used in Examples 20 to 24 and Comparative Examples 13 to 16 were shown in Table 3.

TABLE 3

|  |  | Example 20 | Example 21 | Example 22 | Example 23 | Example 24 | Comparative Example 13 | Comparative Example 14 | Comparative Example 15 | Comparative Example 16 |
|---|---|---|---|---|---|---|---|---|---|---|
| Short fiber (1) | Fiber length | 5 | 3 | 10 | 5 | 5 | 3 | 10 | 0.5 | 90 |
|  | Fineness | 1.1 | 1.1 | 2.0 | 1.7 | 1.7 | 0.5 | 5.0 | 1.1 | 2.0 |
|  | Weight per unit area | 20 | 20 | 30 | 30 | 10 | 20 | 20 | 20 | 20 |
| Long fiber (ground fabric) | Fineness | 56 | 56 | 56 | 56 | 84 | 56 | 56 | 56 | 56 |
|  | Twist number | 1000 | 1000 | 1000 | 1000 | 800 | 1000 | 1000 | 1000 | 1000 |
|  | Twist constant | 7483 | 7483 | 7483 | 7483 | 7332 | 7483 | 7483 | 7483 | 7483 |
|  | Weight per unit area | 40 | 40 | 40 | 40 | 60 | 40 | 40 | 40 | 40 |
| Short fiber (2) | Fiber length | 5 | 3 | 3 | 3 | 3 | 3 | 10 | 0.5 | 90 |
|  | Fineness | 1.1 | 1.1 | 0.8 | 1.1 | 1.1 | 0.5 | 5.0 | 1.0 | 2.0 |
|  | Weight per unit area | 20 | 20 | 10 | 10 | 10 | 20 | 20 | 20 | 20 |
| Weight per unit area of aggregate-removing filter material |  | 80 | 80 | 80 | 80 | 80 | 80 | 80 | 80 | 80 |
| Elongation |  | <1 | <1 | <1 | <1 | <1 | <1 | <1 | <1 | <1 |
| Evaluation | Flow rate change ratio | 0.68 | 0.64 | 0.72 | 0.74 | 0.58 | 0.37 | 0.41 | 0.44 | 0.15 |
|  | Residual leukocyte count | <$10^5$ | <$10^5$ | <$10^5$ | <$10^5$ | <$10^5$ | <$10^5$ | <$10^5$ | <$10^5$ | <$10^5$ |

Fiber length: mm,
Fineness: dtex,
Weight per unit area: g/m$^2$,
Ground fabric total fineness: dtex (12 filaments),
Twist number: turns/m,
Elongation: %

INDUSTRIAL APPLICABILITY

The aggregate-removing filter material according to the present embodiment and the method of filtering a blood product using the aggregate-removing filter material and a leukocyte-removing filter material may be usefully applicable in the medical field.

The invention claimed is:

1. An aggregate-removing filter material for removing aggregates contained in a blood product, comprising short fibers having a fineness of 0.7 to 4.0 dtex and a fiber length of 20 to 60 mm, and a ground fabric comprising longer fibers that are longer than the short fibers, of which a fiber axis is oriented in a planar direction of the ground fabric, wherein the short fibers are entangled with the ground fabric so that the aggregate-removing filter material has a total weight per unit area of 10 to 80 g/m$^2$, a layer of the short fibers forms a three-dimensional structure, and wherein the short fibers and the longer fibers are formed of a synthetic polymer.

2. The aggregate-removing filter material according to claim 1, wherein the ground fabric has a weight per unit area of 5 g/m$^2$ or more.

3. The aggregate-removing filter material according to claim 1, wherein the ratio of the weight per unit area of the ground fabric to the weight per unit area of the short fibers is 1:0.1 to 1:10.

4. The aggregate-removing filter material according to claim 1, wherein the ratio of fineness of the longer fibers to fineness of the short fibers is 1:0.5 to 1:2.

5. The aggregate-removing filter material according to claim 1, wherein the longer fibers are spunbond fibers.

6. The aggregate-removing filter material according to claim 1, wherein the short fibers are entangled with the ground fabric by a spunlace method.

7. The aggregate-removing filter material according to claim 1, the aggregate-removing filter material has an airflow resistance of 4 to 11 Pa·s·m/g.

8. The aggregate-removing filter material according to claim 1, the aggregate-removing filter material comprising a two-layer structure that includes a layer of the longer fibers and a layer of the short fibers.

9. The aggregate-removing filter material according to claim 1, further comprising a three-layer structure that includes a layer of the longer fibers and layers of the short fibers laid on both surfaces of the layer of the longer fibers.

10. The aggregate-removing filter material according to claim 1, wherein the synthetic polymer is selected from the group consisting of polyamide, polyester, polyacrylonitrile, polyurethane, polyvinyl formal, polyvinyl acetal, polytrifluorochloroethylene, poly(meth)acrylate, polysulfone, polystyrene, polyethylene, polypropylene, cellulose, and cellulose acetate.

11. The aggregate-removing filter material according to claim 1, wherein the fineness of the short fibers is 1.2 to 1.8 dtex.

12. A method of filtering a blood product comprising filtering a blood product using a filter apparatus that includes an aggregate-removing filter material and a leukocyte-removing filter material, wherein the aggregate-removing filter material is produced by entangling short fibers having a fineness of 0.7 to 4.0 dtex and a fiber length of 20 to 60 mm with a ground fabric comprising longer fibers that are longer than the short fibers, of which a fiber axis is oriented in a planar direction of the ground fabric to obtain the aggregate-removing filter material having a total weight per unit area of 10 to 80 g/m$^2$, and wherein the short fibers and the longer fibers are formed of a synthetic polymer.

13. The method according to claim 12, wherein the aggregate-removing filter material has a three-dimensional structure formed with a layer of the short fibers which are entangled.

14. The method according to claim 12, wherein the leukocyte-removing filter material has an airflow resistance of 250 to 700 Pa·s·m/g.

15. The method according to claim 12, wherein a fiber structure of the leukocyte-removing filter material has a fineness of 0.001 to 0.07 dtex.

16. The method according to claim 12, wherein the blood product is one that has been stored at 1 to 6° C. for 12 to 80 hours.

17. The method according to claim 16, wherein the blood product is a whole blood product or a concentrated erythrocyte product.

18. The method according to claim 12, wherein the synthetic polymer is selected from the group consisting of polyamide, polyester, polyacrylonitrile, polyurethane, polyvinyl formal, polyvinyl acetal, polytrifluorochloroethylene, poly(meth)acrylate, polysulfone, polystyrene, polyethylene, polypropylene, cellulose, and cellulose acetate.

19. The method according to claim 12, wherein the fineness of the short fibers is 1.2 to 1.8 dtex.

* * * * *